(12) United States Patent
Kawaragi et al.

(10) Patent No.: US 6,489,474 B1
(45) Date of Patent: Dec. 3, 2002

(54) PROCESS FOR PRODUCING AMIDE COMPOUND

(75) Inventors: Yuuji Kawaragi, Kanagawa (JP); Tohru Setoyama, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/926,816

(22) PCT Filed: Apr. 20, 2001

(86) PCT No.: PCT/JP01/03388

§ 371 (c)(1), (2), (4) Date: Dec. 21, 2001

(87) PCT Pub. No.: WO01/81302

PCT Pub. Date: Nov. 1, 2001

(30) Foreign Application Priority Data

Apr. 21, 2000 (JP) ........................................ 2000-121619
Dec. 7, 2000 (JP) ........................................ 2000-372302

(51) Int. Cl.$^7$ ...................... C07D 201/04; C07D 201/08
(52) U.S. Cl. ........................ 540/535; 540/464; 540/539; 548/543; 548/552; 564/215; 564/216; 564/218
(58) Field of Search ................................ 564/215, 216, 564/218; 540/464, 535, 539; 548/543, 552

(56) References Cited

FOREIGN PATENT DOCUMENTS

| DE | 35 38 859 | 5/1987 |
|---|---|---|
| EP | 0 461 779 | 12/1991 |
| EP | 0 515 063 | 11/1992 |

OTHER PUBLICATIONS

Yusuke Izumi "Catalytic Beckmann Rearrangement of Oximes in Homogenous Liquid Phase" Chemistry Letters 1990 pp. 2171–2174.

Hiroshi Sato, Hiroshi Yoshioka, Yusuke Izumi "Homogeneous liquid–phase Beckmann rearrangement of oxime catalyzed by phosphorus pentaoxide and accelerated by fluorine–containing strong acid" Journal of Molecular Catalysis A: Chemical 149 (1999) 25–32 Feb. 25, 1999 pp. 25–32.

Yusuke Izumi, Tomokazu Fujita "Iminium salt–catalyzed liquid–phase Beckmann rearrangement of cyclohexanone oxime" Journal of Molecular Catalysis A: Chemical 106 (1996) 43–49 Oct. 2, 1995 pp. 43–49.

Primary Examiner—Shailendra Kumar
(74) Attorney, Agent, or Firm—Oblon, Spivak, McClelland, Maier & Neustadt, P.C.

(57) ABSTRACT

Object of the present invention is to provide a process for producing an amide compound with high efficiency by subjecting an oxime compound to Beckmann rearrangement in a liquid phase under mild reaction conditions. Namely, the invention relates to a process for producing an amide compound such as ε-caprolactam by subjecting an oxime compound such as cyclohexanone oxime to Beckmann rearrangement in a liquid phase, characterized in that the reaction is carried out in the presence of (1) a non-fluorine-containing sulfonic anhydride and an N,N-disubstituted amide compound or (2) at least one compound selected from the group consisting of sulfonic acids and anhydrides thereof, an N,N-disubstituted amide compound, and a carboxylic anhydride.

27 Claims, No Drawings

PROCESS FOR PRODUCING AMIDE COMPOUND

This application is a 371 of PCT/JP01/03388 filed Nov. 20, 2001.

TECHNICAL FIELD

The present invention relates to a process for producing an amide compound. More specifically, it relates to a process for producing an amide compound effectively by carrying out Beckmann rearrangement of an oxime in a liquid phase in the presence of a catalyst.

BACKGROUND OF THE INVENTION

Generally, as an industrial process for producing an amide compound, a process of converting an oxime compound into an amide compound through Beckmann rearrangement. For example, ε-caprolactam is produced through Beckmann rearrangement of cyclohexanone oxime. For such Beckmann rearrangement, currently a liquid-phase reaction has been adopted using a strong acid such as concentrated sulfuric acid or fuming sulfuric acid as the catalyst. However, in this known method, there are problems that, for separating the lactam compound formed, the sulfuric acid should be usually neutralized with ammonia to result in the formation of ammonium sulfate in an amount twice the amount of the above lactam compound as a by-product, and the reaction apparatus is corroded since a large amount of the strong acid is used. Therefore, the process is not necessarily economical and thus, it is expected to develop an effective catalyst for the rearrangement.

Therefore, Beckmann rearrangement in liquid phase has been variously investigated without using the sulfuric acid catalyst. For example, the following process are proposed for Beckmann rearrangement of cyclohexanone oxime in liquid phase using homogeneous catalysts: a process using an ion pair obtainable by reacting N,N-dimethylformamide with chlorosulfonic acid (a Vilsmeier complex), as the catalyst [M. A. Kira and Y. M. Shaker, Egypt. J. Chem., 16, 551 (1973)]; a process using a catalyst composed of an N,N-dialkylformamide and an alkylating agent obtainable from an epoxy compound and a strong acid (boron trifluoride-etherate or the like) [Y. Izumi, Chemistry Letters, pp. 2171 (1990)]; a process of rearranging cyclohexanone oxime with a phosphoric acid or a condensed phosphoric acid compound in a heptane solvent (Japanese Patent Laid-Open No. 149665/1987); a process using a catalyst composed of phosphorus pentoxide and a fluorine-containing strong acid or its derivative and a compound such as N,N-dialkylformamide (Japanese Patent Laid-Open No. 105654/1993; corresponding to U.S. Pat. No. 5,254,684); and the like.

However, the processes for producing ε-caprolactam by subjecting cyclohexanone oxime to Beckmann rearrangement in a liquid phase using these catalyst systems are not always satisfactory as industrial processes. Specifically, in the above Beckmann rearrangement of cyclohexanone oxime using a Vilsmeier complex as the catalyst, the lactam produced and the catalyst form a 1:1 complex, so that it is necessary to use the catalyst in an amount equimolar to the starting oxime. For this reason, the process cannot be said to be an economical industrial process. The process using a catalyst composed of an N,N-dialkylformamide and an alkylating agent obtained from an epoxy compound and a strong acid shows a novel method for the rearrangement, which is different from the conventional equimolar reaction using sulfuric acid as the catalyst. However, it is industrially not always satisfactory in view of operability because toxic compounds such as dimethyl sulfate and epichlorohydrin are sometimes used for producing the alkylating agent which is one of the rearrangement catalyst components. Further, in the process using phosphoric acid or a condensed phosphoric acid as the catalyst disclosed in Japanese Patent Laid-Open No. 149665/1987, the phosphoric acid catalyst is required in an amount as large as about 2 mol per 1 mol of the starting oxime, so that the process results in a large load on the catalyst-neutralizing step with ammonia after the reaction. Therefore, the process cannot be said to be economical industrial process.

In the process using a catalyst composed of phosphorus pentoxide and a fluorine-containing strong acid (e.g., a fluorine-containing sulfonic anhydride) or its derivative and a compound such as N,N-dialkylformamide disclosed in the above Japanese Patent Laid-Open No. 105654/1993 (U.S. Pat. No. 5,254,684), the catalyst shows a high catalytic activity but the specification describes that the catalytic activity is deactivated by the action of a trace amount of water, so that it is necessary to remove moisture strictly from the starting oxime, a reaction solvent, a reaction apparatus, and the like. In particular, the phosphorus pentoxide compound, a component of the catalyst, is known as a strong dehydrating agent by those skilled in the art, and thus, owing to the extremely high hygroscopicity, the handling is accompanied by a considerable care and troublesomeness. In addition, trifluoromethanesulfonic anhydride (a fluorine-containing strong acid compound) for use as a constituting component of the catalyst is effective as a highly active component of the catalyst, but is expensive and causes a problem of corrosion of the apparatus.

As described above, the catalyst systems heretofore proposed are not always satisfactory for the industrial production in view of catalyst efficiency, handling, and economical efficiency.

Object of the present invention is to provide a process for producing an amide compound with high efficiency through Beckmann rearrangement of an oxime compound in a liquid phase in the presence of an acid catalyst, by rearranging the oxime catalytically under a mild reaction conditions and using a small amount of catalyst, which is free from the above problems.

DISCLOSURE OF THE INVENTION

As a result of the extensive studies of catalysts for Beckmann rearrangement of an oxime compound into an amide compound, the present inventors have found that an amide compound can be obtained in a yield as high as in the case of the conventional process by carrying out the rearrangement using a catalyst comprising an aromatic sulfonic anhydride or non-fluorine-containing aliphatic sulfonic anhydride and an N,N-disubstituted amide compound without using an expensive fluorine-containing strong acid compound which is heretofore considered to be essential as a constituting component of the catalyst, and have attained the present invention.

Also, they have found that an amide compound can be obtained with higher efficiency by carrying out the rearrangement in the presence of at least one compound selected from the group consisting of sulfonic acids and anhydrides thereof, an N,N-disubstituted amide compound, and a carboxylic anhydride, and have attained the invention.

Namely, the first gist of the invention lies in a process for producing an amide compound by subjecting an oxime compound to Beckmann rearrangement in a liquid phase, characterized in that the reaction is carried out in the presence of a non-fluorine-containing sulfonic anhydride and an N,N-disubstituted amide compound.

The second gist of the invention lies in a process for producing an amide compound by subjecting an oxime compound to Beckmann rearrangement in a liquid phase, characterized in that the rearrangement is carried out in the presence of at least one compound selected from the group consisting of sulfonic acids and anhydrides thereof, an N,N-disubstituted amide compound, and an carboxylic anhydride.

As the preferred embodiments of the first gist of the invention, in the above process for producing an amide compound, it may be mentioned that the sulfonic anhydride is a non-fluorine-containing sulfonic anhydride, for example, a non-fluorine-containing benzenesulfonic anhydride or a non-fluorine-containing alkylsulfonic anhydride which may have a substituent, particularly p-toluenesulfonic anhydride or methanesulfonic anhydride, and the N,N-disubstituted amide compound is N,N-dimethylformamide, as well as the oxime compound is cyclohexanone oxime and the amide compound is ε-caprolactam.

As the preferred embodiments of the second gist of the invention, in the above process for producing an amide compound, it may be mentioned that the sulfonic acids are aromatic sulfonic acids or aliphatic sulfonic acids, for example, benzenesulfonic acids or alkylsulfonic acids which may have a substituent, at least one compound selected from the group consisting of sulfonic acids and anhydrides thereof is p-toluenesulfonic anhydride, methanesulfonic anhydride, p-toluenesulfonic acid, or methanesulfonic acid, the N,N-disubstituted amide compound is N,N-dimethylformamide, and the carboxylic anhydride is acetic anhydride, as well as the oxime compound is cyclohexanone oxime and the amide compound is ε-caprolactam.

BEST MODE FOR CARRYING OUT THE INVENTION

The following will explain the detail of the present invention.
(Oxime Compound)

Any known oxime compound can be used, without limitation, as the starting oxime compounds to be used in Beckmann rearrangement in the present invention. Specific examples of the oxime compound include oxime compounds having 2 to 20 carbon atoms, preferably 3 to 13 carbon atoms, such as cyclohexanone oxime, cyclopentanone oxime, cyclododecanone oxime, acetone oxime, 2-butanone oxime, acetophenone oxime, benzophenone oxime, 4'-hydroxyacetophenone oxime and the like. Among them, cyclic oxime compounds having 4 to 20 carbon atoms, preferably 5 to 13 carbon atoms, such as cyclohexanone oxime, cyclopentanone oxime, cyclododecanone oxime, and the like are preferably used.
(Catalyst for the First Gist)

The catalyst for the rearrangement to be used in the invention of first gist of the present invention contains a non-fluorine-containing sulfonic anhydride and an N,N-disubstituted amide compound as constituting components. In present, it is not clear what form of an active species of catalyst is formed from these catalyst-constituting components. However, since the reaction proceeds by the action of the starting oxime compound, the starting oxime compound can be considered to be one component of the catalyst-constituting components.

Non-fluorine-containing Sulfonic Anhydride

The non-fluorine-containing sulfonic anhydride to be used as a constituting component of the present catalyst is not particularly limited and includes a non-fluorine-containing aromatic sulfonic anhydride or a non-fluorine-containing linear or cyclic aliphatic sulfonic anhydride. A non-fluorine-containing aromatic sulfonic anhydride having 6 to 20 carbon atoms, preferably 6 to 10 carbon atoms which may have one or more substituents on the aromatic ring or a non-fluorine-containing aliphatic sulfonic anhydride having 1 to 20 carbon atoms, preferably 1 to 10 carbon atoms which may have a substituent can be used (wherein the substituent represents an alkyl group having 1 to 8 carbon atoms, an alkoxy group having 1 to 4 carbon atoms, an acyl group having 2 to 4 carbon atoms, and a halogen atom such as Cl or Br). The valence number of the non-fluorine-containing sulfonic anhydride is not particularly limited but has preferably a valence number of 1.

Specific examples include benzenesulfonic anhydride, p-toluenesulfonic anhydride, m-xylene-4-sulfonic anhydride, p-dodecylbenzenesulfonic anhydride, 2,4-dimethylbenzenesulfonic anhydride, 2,5-dimethylbenzenesulfonic anhydride, 4-chlorobenzenesulfonic anhydride, α-naphthylsulfonic anhydride, β-naphthylsulfonic anhydride, biphenylsulfonic anhydride, methanesulfonic anhydride, ethanesulfonic anhydride, propanesulfonic anhydride, 1-hexanesulfonic anhydride, 1-octanesulfonic anhydride, and the like. Among them, preferred is a non-fluorine-containing benzenesulfonic anhydride or alkylsulfonic anhydride, particularly preferred is p-toluenesulfonic anhydride or methanesulfonic anhydride.

The rearrangement proceeds when a fluorine-containing aromatic sulfonic anhydride is used instead of a non-fluorine-containing sulfonic anhydride which is a constituting component of the catalyst for the rearrangement to be used in the invention. However, as mentioned above, since the fluorine-containing strong acid compound is extremely expensive, it is essential to establish a technology of recovering and re-using the fluorine-containing strong acid compound for establishing an economical industrial production process.

The amount of the non-fluorine-containing sulfonic anhydride to be used in the invention is not particularly limited but, in general, the compound is used in an amount ranging from about 0.2 to 20 mol %, preferably 1.0 to 15 mol %, more preferably 2.0 to 12 mol % based on the starting oxime. When the amount is smaller than the range, a sufficient catalytic activity cannot be attained, while use of too large amount requires much load for treating the catalyst after the rearrangement. Thus, both are not preferred.
N,N-Disubstituted Amide Compound The N,N-disubstituted amide compound to be used in the catalyst system of the invention is generally a carbamide, especially formamide having the same or different alkyl groups having 1 to 18 carbon atoms, preferably 1 to 8 carbon atoms, more preferably 1 to 4 carbon atoms on the nitrogen atom. Examples of the substituents on the nitrogen atom include an alkyl group, an alkoxy group, an aryl group and the like. Among them, an alkyl group is preferred and an amide compound having no cyclic structure containing the nitrogen atom is preferred. Specific examples of the compound include N,N-dimethylformamide, N,N-diethylformamide, N,N-di-i-propylformamide, N,N-dibutylformamide, N,N-dipentylformamide, N,N-dioctylformamide, N-methyl-N-stearylformamide, dimethylacetamide, diethylacetamide, and the like. Among them, a compound in which two alkyl groups are the same is preferred and particularly preferred is N,N-dimethylformamide.

The amount of the above N,N-disubstituted amide compound to be used is not particularly limited, and the amount varies with the amount range of the starting oxime compound used and the amount range of the catalyst to be combined, such as sulfonic anhydride and therefore, is not determined uniformly. However, the amide compound is generally used in an amount of 1 to 1000 times by weight, preferably 2 to 100 times, more preferably 4 to 50 times, by weight as much as the oxime compound. Also, the amide compound is used in a molar ratio of generally 10 to 2000, preferably 25 to 1000, more preferably 50 to 500 relative to the non-fluorine-containing sulfonic anhydride.

The N,N-disubstituted amide compound to be used in the invention is a constituting component of the catalyst but also acts as a solvent at the same time. Therefore, in the case that suitable other solvent is used for smooth proceeding of the rearrangement, the amide compound can be used in combination with the solvent.

(Catalyst for the Second Gist)

The catalyst for the rearrangement used in the invention of first gist of the present invention contains a non-fluorine-containing sulfonic anhydride and an N,N-disubstituted amide compound as constituting components. In the invention of the second gist of the present invention, however, an amide compound can be produced in higher yields under mild conditions by using a catalyst containing at least one compound selected from sulfonic acids and anhydrides thereof, an N,N-disubstituted amide compound, and a carboxylic anhydride as constituting components.

At least One Compound Selected from Sulfonic Acids and Anhydrides Thereof

As the sulfonic acid or its anhydride, at least one compound selected from aromatic sulfonic acids, linear or cyclic aliphatic sulfonic acid and anhydrides thereof may be mentioned without particular limitation. An aromatic sulfonic acid having 6 to 20 carbon atoms which may have one or more substituents on the aromatic ring (e.g., benzenesulfonic acid), an aliphatic sulfonic anhydride having 1 to 20 carbon atoms which may have a substituent (e.g., an alkylsulfonic acid) and anhydrides thereof can be used (wherein the substituent represents an alkyl group having 1 to 12 carbon atoms, an alkoxy group having 1 to 4 carbon atoms, an acyl group having 2 to 4 carbon atoms, and a halogen atom such as Cl, Br, F etc.). The valence number of the compound is not particularly limited but it has preferably a valence number of 1.

Specific examples include benzenesulfonic acid, p-toluenesulfonic acid, p-toluenesulfonic acid monohydrate, p-dodecylbenzenesulfonic acid, 2,4-dimethylbenzenesulfonic acid, 2,5-dimethylbenzenesulfonic acid, 4-chlorobenzenesulfonic acid, 4-fluorobenzenesulfonic acid, α-naphthylsulfonic acid, β-naphthylsulfonic acid, biphenylsulfonic acid, methanesulfonic acid, trifluoromethanesulfonic acid, ethanesulfonic acid, propanesulfonic acid, 1-hexanesulfonic acid, 1-octanesulfonic acid, and anhydrides thereof, and the like. Among them, preferred are methanesulfonic acid, trifluoromethanesulfonic acid, ethanesulfonic acid, propanesulfonic acid, benzenesulfonic acid, p-toluenesulfonic acid, p-dodecylbenzenesulfonic acid, and anhydrides thereof, and particularly preferred are methanesulfonic acid, trifluoromethanesulfonic acid, p-toluenesulfonic acid and anhydrides thereof. The catalyst of the second gist of the present invention uses a carboxylic anhydride, which remarkably increases the catalyst activity and reduces the cost of the catalyst. In such as case, a fluorine-containing sulfonic acid compound may be used as the sulfonic acid or the anhydride thereof but it is more preferable to use a non-fluorine-containing sulfonic acid compound to further reduce the cost of the catalyst.

The amount of the at least one compound selected from sulfonic acids and anhydrides thereof in the invention is not particularly limited but, in general, the compound is used in the range of about 0.2 to 20 mol %, preferably 1.0 to 15 mol %, more preferably 2.0 to 12 mol % to the starting oxime. When the amount is smaller than the range, a sufficient catalytic activity cannot be attained, while use of too large amount requires much load for treating the catalyst after the rearrangement. Thus, both are not preferred.

N,N-Disubstituted Amide Compound

As the N,N-disubstituted amide compound to be used in the catalyst system of the second gist of the present invention, a similar kind and amount to those of the N,N-disubstituted amide compound in the catalyst system of the first gist mentioned above can be used. The amount to be used is in the range of a molar ratio of generally 10 to 2000, preferably 25 to 1000, more preferably 50 to 500 relative to the sulfonic acid and its anhydride.

Carboxylic Anhydride

The carboxylic anhydride to be used in the catalyst system of the invention is not particularly limited and an aliphatic carboxylic anhydride having 1 to 20 carbon atoms, preferably 1 to 8 carbon atoms which may have a substituent or an aromatic carboxylic anhydride having 6 to 12 carbon atoms which may have a substituent can be used (wherein the substituent represents an alkyl group having 1 to 12 carbon atoms, an alkoxy group having 1 to 4 carbon atoms, an acyl group having 2 to 4 carbon atoms, a halogen atom such as Cl, Br, F etc.). The valence number of the carboxylic anhydride is not particularly limited but it has preferably a valence number of 1. Specific examples include acetic anhydride, propionic anhydride, n-butyric anhydride, n-valeric anhydride, n-caproic anhydride, n-heptanoic-anhydride, 2-ethylbexanoic anhydride, benzoic anhydride, phthalic anhydride, maleic anhydride, succinic anhydride, and the like. Among them, preferred is an alkylcarboxylic anhydride having 1 to 4 carbon atoms, particularly preferred are acetic anhydride and propionic anhydride which are compounds having low boiling points, and most preferred is acetic anhydride.

The amount of the carboxylic anhydride to be used in the invention is not particularly limited, but in general, the compound is generally used in the range of molar equivalent of about 0.5 to 200, preferably 1.0 to 100, more preferably 2.0 to 50 to the at least one compound selected from the group consisting of the above aromatic sulfonic acids, aliphatic sulfonic acids and anhydride thereof. When the amount is smaller than the range, a sufficient catalytic activity cannot be attained, while use of too-large amount requires much load for separating the catalyst after the rearrangement.

(Solvent)

Examples of the solvent to be used in the rearrangement of the invention other than the N,N-disubstituted amide compound include aliphatic hydrocarbon compounds such as n-hexane, n-heptane, n-octane, and n-dodecane; aromatic hydrocarbon compounds such as benzene, toluene, xylene, mesitylene, monochlorobenzene, and methoxybenzene; nitrile compounds such as acetonitrile, propanenitrile, capronitrile, adiponitrile, benzonitrile, and tolunitrile; ester compounds such as dimethyl phthalate, dibutyl phthalate, dimethyl malonate, and dimethyl succinate; and the like. Aromatic hydrocarbon compounds are preferred in view of enhancing the solubility of the starting oxime and the catalyst components. They may be used alone or as a mixture.

In the case of using a solvent other than the N,N-disubstituted amide compound, the solvent may be mixed in an amount of 0.001 to 20 times by volume, preferably 0.1 to 10 times by volume, more preferably 0.5 to 1 times by volume as much as the N,N-disubstituted amide compound. The mixing within such a range can reduce the load at the separation by distillation of the N,N-disubstituted amide compound after the reaction.

(Reaction Conditions)

The conditions for carrying out the process of the present invention are not particularly limited but the reaction is carried out at a temperature ranging generally from 0 to 200° C., preferably from 40 to 150° C., more preferably from 60 to 130° C. The reaction pressure is also not particularly limited and the reaction is carried out under a pressure ranging from normal pressure to enhanced pressure. The reaction time or residence time is generally from 10 seconds to 10 hours, preferably 1 minute to 7 hours.

In the invention, the rearrangement proceeds even when each catalyst component and the starting oxime compound are mixed in any order. In the case of the catalyst system of the first gist, for example, it is preferred that the non-fluorine-containing sulfonic anhydride and the N,N-disubstituted amide compound are mixed and heated at a predetermined temperature, and then a raw material solution in which the oxime is dissolved is fed gradually thereto to start the reaction. In the case of the second catalyst system, for example, it is preferred that at least one compound selected from the group consisting of sulfonic acids and anhydrides thereof and the carboxylic anhydride are added to the N,N-disubstituted amide compound, and the resulting mixture as it is or after addition of a small amount of a starting oxime is heated at a predetermined temperature, followed by gradual feeding of a raw material solution in which the oxime is dissolved thereto to start the reaction.

In that case, the starting oxime compound can be provided as a solution dissolved in a part of the N,N-disubstituted amide compound. It is not preferred to start the reaction at such a state that a high concentration of the oxime compound is present in the above catalyst component solution by feeding the starting oxime compound all at once because early deactivation of the catalyst and increase of by-products may be invited.

(Reaction Mode)

The reaction mode for carrying out the reaction of the invention is not particularly restricted and both of a batch reaction and a continuous flow reaction can be carried out, but a continuous flow reaction mode is preferably used in the industrial production. The type of the reactor is not particularly limited and a general reactor such as a reactor composed of one tank or two or more continuous tanks, a tubular reactor, or the like may be used. Since an acid catalyst is used in the invention, the material to be used for the reactor is preferably a corrosion resistant material. Examples thereof include stainless steel, Hastelloy, Monel, Inconel, titanium, a titanium alloy, zirconium, a zirconium alloy, nickel, a nickel alloy, tantalum, or a fluorine resin, a variety of glass materials whose inside are coated, and the like.

It is preferred that the starting oxime compound, the catalyst components, and the reaction solvent to be used in the reaction are provided into the reaction after prior thorough removal of moisture in view of attaining a high catalytic activity and a high selectivity to the amide compound.

With regard to the reaction mode of the first gist of the invention, the following will explain specifically by reference to an example of a continuous flow reaction.

An N,N-disubstituted amide compound solution in which a non-fluorine-containing sulfonic anhydride is dissolved and an N,N-disubstituted amide compound solution in which a starting oxime compound is dissolved are continuously fed to an reactor, if necessary, together with an inert solvent, and they are allowed to react during a desired residence time. At the same time, a reaction mixture containing an amide compound formed, unreacted oxime compound, and the catalyst components is continuously taken out. In the case of the second gist of the invention, a continuous flow reaction can be carried out in a similar manner to the reaction mode of the above first gist of the invention with the exception that an N,N-disubstituted amide compound in which at least one compound selected from the group consisting of sulfonic acids and anhydrides thereof and a carboxylic anhydride are dissolved is provided.

(Treatment After the Reaction)

The reaction mixture taken out contains low-boiling by-products, the solvent, a carboxylic acid (in the case that a carboxylic anhydride is used), the N,N-disubstituted amide compound, the objective amide compound, unreacted oxime, and remaining catalyst components. The reaction mixture is then introduced into a distillation column to remove successively the low-boiling by-products, the solvent such as toluene, the carboxylic acid (in the case that a carboxylic anhydride is used), and the N,N-disubstituted amide compound which is one of the catalyst components by distillation, whereby a mixture containing the amide compound of the objective product, the unreacted oxime compound, and the catalyst components is obtained. The recovered inert solvent and the N,N-disubstituted amide of a catalyst-constituting component can be recycled into the reactor, but in that case, unnecessary by-products are separately removed by separation with a separating means such as distillation.

The mixture containing the amide compound of the objective product, the unreacted oxime compound, and the remaining catalyst components is, for example, neutralized by adding an aqueous solution of an alkali compound such as $NH_3$ or NaOH to deactivate the catalyst and then a solvent such as toluene is added thereto as a negative solvent to precipitate the deactivated catalyst as solids, whereby it is effected to separate the amide compound of the objective product and the oxime compound from the catalyst. Then, the mixture of the solvent, the objective amide compound, and the oxime compound is separated into the inert solvent and the objective amide compound and the oxime compound by means of any of various separating operations such as separation by distillation, separation by extraction, separation by crystallization, or the like. The recovered inert solvent can be recycled into the reactor, but in that case, unnecessary by-products are separately removed by separation with a separating means such as distillation. A more highly pure product of the objective amide compound can be obtained by purification through further introducing the compound into a distillation column.

The catalyst salt deactivated and separated by adding an alkali compound such as $NH_3$ or NaOH, for example, an aromatic sulfonate salt can be easily converted into the corresponding sulfonic acid with, for example, an strong acid such as sulfuric acid, hydrochloric acid, or nitric acid, or a solid acid, an acid-form ion exchange-resin, or the like. The regenerated sulfonic acid compound can be converted into the corresponding sulfonic anhydride through easy dehydration under mild conditions, for example, by contacting with a dehydrating agent such as fuming sulfuric acid, diphosphorus pentoxide, or condensed phosphoric acid. The regenerated sulfonic acid or sulfonic anhydride can be recycled to the reactor, optionally together with an inert solvent.

EXAMPLES

The present invention will be explained specifically by reference to Examples, but the invention is not limited to these Examples unless it exceeds the gist.

Incidentally, in the following Examples, the yields of the lactam are represented by mol % based on the charged oxime compound. The values of TON (Turn Over Number) are represented by mol of the formed lactam based on mol of the charged sulfonic acid or sulfonic anhydride.

Example 1

A 50 ml, round-bottomed flask dried in a dryer at 100° C. was purged with a dry nitrogen treated with molecular sieves 4A, and then 10 ml of N,N-dimethylformamide dried beforehand with molecular sieves 4A, 0.10 g of n-tetradecane (an internal standard substance for gas chromatography), and 97.6 mg (0.30 mmol; 3.4 mol % based on oxime) of p-toluenesulfonic anhydride were added thereto, followed by stirring under heating at 110° C. for 10 minutes. Then, a solution of 1.00 g (8.84 mmol) of cyclohexanone oxime dissolved in 10 ml of N,N-dimethylformamide was added thereto and the reaction was carried out at 110° C. for 15 minutes. After completion of the reaction, the reaction solution was treated with a commercial aqueous solution of 28% $NH_3$ to deactivate the catalyst. The reaction solution after the deactivation was analyzed by gas chromatography. The result showed that the yield of ε-caprolactam is 85.9% and the value of TON is 25.2.

Comparative Example 1

Beckmann rearrangement of cyclohexanone oxime was carried out in a similar manner to Example 1 with the exception that 114.1 mg (0.60 mmol; 6.8 mol % based on oxime) of p-toluenesulfonic acid monohydrate was used instead of p-toluenesulfonic anhydride. The result showed that the yield of ε-caprolactam is 1.7% and the value of TON is 0.3.

Comparative Example 2

Beckmann rearrangement of cyclohexanone oxime was carried out in a similar manner to Example 1 with the exception that 103.3 mg (0.60 mmol) of p-toluenesulfonic acid (no water of crystallization) was used instead of p-toluenesulfonic anhydride. The result showed that the yield of ε-caprolactam is 3.3% and the value of TON is 0.5.

Comparative Example 3

Beckmann rearrangement of cyclohexanone oxime was carried out in a similar manner to Example 1 with the exception that chlorobenzene was used as the solvent instead of N,N-dimethylformamide. The result showed that the yield of ε-caprolactam is 8.0% and the value of TON is 2.3.

Examples 2 to 3

Each Beckmann rearrangement of cyclohexanone oxime was carried out in a similar manner to Example 1 with the exception that the reaction was carried out at a temperature shown in Table 1.

Table 1 shows the results of Examples 1 to 3 and Comparative Examples 1 to 3.

TABLE 1

| | Sulfonic acid anhydride | Di-substituted amide | Reaction temperature (° C.) | Yield of lactam (%) | Value of TON |
|---|---|---|---|---|---|
| Example 1 | p-toluene-sulfonic anhydride | DMF | 110 | 85.9 | 25.2 |
| Comparative Example 1 | none (p-toluene-sulfonic acid monohydrate) | DMF | 110 | 1.7 | 0.3 |
| Comparative Example 2 | none (p-toluene-sulfonic acid) | DMF | 110 | 3.3 | 0.5 |
| Comparative Example 3 | p-toluene-sulfonic anhydride | chloro-benzene | 110 | 8.0 | 2.3 |
| Example 2 | p-toluene-sulfonic anhydride | DMF | 80 | 70.5 | 20.7 |
| Example 3 | p-toluene-sulfonic anhydride | DMF | 130 | 66.9 | 19.8 |

Example 4

A 50 ml, round-bottomed flask dried in a dryer at 100° C. was purged with a dry nitrogen treated with molecular sieve 4A, and then, 0.75 g (2.30 mmol; 13 mol % based on oxime) of p-toluenesulfonic anhydride, 0.10 g of n-tetradecane (an internal standard substance for gas chromatography) dried beforehand with molecular sieve 4A, and 5 ml of N,N-dimethylformamide were added thereto, and the resulting mixture was heated to 74° C. under stirring. Then, a solution of 2.00 g (17.67 mmol) of cyclohexanone oxime dissolved in 5 ml of N,N-dimethylformamide was added thereto over a period of 10 minutes to effect the rearrangement. After completion of the reaction, the reaction solution was treated with a commercial aqueous solution of 28% $NH_3$ to deactivate the catalyst. Thereafter, the reaction solution was analyzed by gas chromatography. The result showed that the yield of ε-caprolactam is 95.8% and the value of TON is 7.4.

Example 5

Beckmann rearrangement of cyclohexanone oxime was carried out in a similar manner to Example 4 with the exception that a mixed liquid of N,N-dimethylformamide/toluene (80/20; % by volume) was used instead of N,N-dimethylformamide (100% by volume). The result showed that the yield of ε-caprolactam is 95.2% and the value of TON is 7.3.

Example 6

Beckmann rearrangement of cyclohexanone oxime was carried out in a similar manner to Example 4 with the exception that a mixed liquid of N,N-dimethylformamide/toluene (50/50% volume ratio) was used instead of N,N-dimethylformamide (100% by volume). The result showed that the yield of ε-caprolactam is 94.4% and the value of TON is 7.3.

Table 2 shows the results of Examples 4 to 6.

TABLE 2

|  | DMF/toluene volume ratio | Yield of lactam (%) | value of TON |
|---|---|---|---|
| Example 4 | DMF 100% | 95.8 | 7.4 |
| Example 5 | 80/20 | 95.2 | 7.3 |
| Example 6 | 50/50 | 94.4 | 7.3 |

Example 7

A 50 ml, round-bottomed flask dried in a dryer at 100° C. was purged with a dry nitrogen treated with molecular sieve 4A, and then, 0.600 g (1.838 mmol; 10.8 mol % based on oxime) of p-toluenesulfonic anhydride, 0.10 g of n-tetradecane (an internal standard substance for gas chromatography) dried beforehand with molecular sieve 4A, and 4 ml of N,N-dimethylformamide were added thereto, and the resulting mixture was heated to 74° C. under stirring. Then, a solution of 1.92 g (16.96 mmol) of cyclohexanone oxime dissolved in 4 ml of N,N-dimethylformamide was added thereto over a period of 5 minutes to effect the rearrangement. After completion of the reaction, the reaction solution was treated with a commercial aqueous solution of 28% $NH_3$ to deactivate the catalyst. Thereafter, the reaction solution was analyzed by gas chromatography. The result showed that the yield of ε-caprolactam is 96.3% and the value of TON is 8.8.

Example 8

Beckmann rearrangement of cyclohexanone oxime was carried out in a similar manner to Example 7 with the exception that the amount of p-toluenesulfonic anhydride is changed to 0.304 g (0.931 mmol; 5.5 mol % based on oxime). The result showed that the yield of ε-caprolactam is 66.7% and the value of TON is 12.2.

Example 9

Beckmann rearrangement of cyclohexanone oxime was carried out in a similar manner to Example 8 with the exception that N,N-diethylformamide was used instead of N N-dimethylformamide. The result showed that the yield of ε-caprolactam is 38.4% and the value of TON is 7.0.

Example 10

Beckmann rearrangement of cyclohexanone oxime was carried out in a similar manner to Example 8 with the exception that N,N-dimethylacetamide was used instead of N,N-dimethylformamide. The result showed that the yield of 6-caprolactam is 27.8% and the value of TON is 5.3.

Table 3 shows the results of Examples 7 to 10.

TABLE 3

|  | Amount of p-toluenesulfonic anhydride | Di-substituted amide | Yield of lactam (%) | Value of TON |
|---|---|---|---|---|
| Example 7 | 1.838 mmol | N,N-dimethyl formamide | 96.3 | 8.8 |
| Example 8 | 0.931 mmol | N,N-dimethyl formamide | 66.7 | 12.2 |
| Example 9 | 0.931 mmol | N,N-diethyl formamide | 38.4 | 7.0 |

TABLE 3-continued

|  | Amount of p-toluenesulfonic anhydride | Di-substituted amide | Yield of lactam (%) | Value of TON |
|---|---|---|---|---|
| Example 10 | 0.931 mmol | N,N-dimethyl acetamide | 27.8 | 5.3 |

Examples 11 to 14

Each Beckmann rearrangement of cyclohexanone oxime was carried out in a similar manner to Example 8 with the exception that a sulfonic anhydride described in Table 4 was used instead of p-toluenesulfonic anhydride. Table 4 shows the results.

TABLE 4

| Example | Sulfonic anhydride | | Yield of caprolactam (%) | Value of TON |
|---|---|---|---|---|
| | Compound | Amount | | |
| 11 | 4-chloro-benzenesulfonic anhydride | 0.338 g (0.92 mmol) | 54.3 | 10.0 |
| 12 | p-dodecyl-benzenesulfonic anhydride | 0.591 g (0.93 mmol) | 35.0 | 6.4 |
| 13 | m-xylene-4-sulfonic anhydride | 0.313 g (0.96 mmol) | 65.0 | 11.5 |
| 14 | methanesulfonic anhydride | 0.185 g (1.06 mmol) | 64.5 | 10.3 |

Example 15

A 50 ml, round-bottomed flask dried in a dryer at 100° C. was purged with a dry nitrogen treated with molecular sieve 4A, and then, 0.309 g( 0.948 mmol) of p-toluenesulfonic anhydride, 0.820 g (8.032 mmol) of acetic anhydride, 0.10 g of n-tetradecane (an internal standard substance for gas chromatography) dried beforehand with molecular sieve 4A, and 4 ml of N,N-dimethylformamide were added thereto, and the resulting mixture was heated to 74° C. under stirring. Then, a solution of 1.92 g (16.96 mmol) of cyclohexanone oxime dissolved in 4 ml of N,N-dimethylformamide was added thereto over a period of 5 minutes to effect the rearrangement. After completion of the reaction, the reaction solution was treated with a commercial aqueous solution of 28% $NH_3$ to deactivate the catalyst. Thereafter, the reaction solution was analyzed by gas chromatography. The result showed that the yield of ε-caprolactam is 96.44% and the value of TON is 17.3.

Examples 16 to 20

Each Beckmann rearrangement of cyclohexanone oxime was carried out in a similar manner to Example 15 with the exception that the amount of p-toluenesulfonic anhydride, the amount of cyclohexanone oxime and acetic anhydride were changed to those described in Table 5. Table 5 shows the results.

TABLE 5

| Example | Amount of sulfonic anhydride | Amount of oxime (mmol) | Carboxylic anhydride Compound | Carboxylic anhydride Amount | Yield of caprolactam (%) | Value of TON |
|---|---|---|---|---|---|---|
| 15 | 0.309 g (0.948 mmol) | 16.96 | acetic anhydride | 0.820 g (8.032 mmol) | 96.44 | 17.3 |
| 16 | 0.149 g (0.457 mmol) | 16.96 | acetic anhydride | 0.820 g (8.032 mmol) | 83.28 | 30.9 |
| 17 | 0.153 g (0.471 mmol) | 17.19 | acetic anhydride | 0.209 g (2.047 mmol) | 77.52 | 28.3 |
| 18 | 0.152 g (0.464 mmol) | 16.96 | acetic anhydride | 0.095 g (0.931 mmol) | 57.38 | 21.0 |
| 19 | 0.309 g (0.948 mmol) | 17.34 | not added | 0 g | 66.7 | 12.2 |
| 20 | 0.149 g (0.457 mmol) | 16.25 | not added | 0 g | 34.59 | 12.3 |

*Sulfonic anhydride: p-toluenesulfonic anhydride

Example 21

Beckmann rearrangement of cyclohexanone oxime was carried out in a similar manner to Example 15 with the exception that a mixed liquid of N,N-dimethylformamide/toluene (50/50% volume ratio) was used instead of N,N-dimethylformamide (100% by volume) and the amount of p-toluenesulfonic anhydride was changed to 0.154 g (0.472 mmol; 2.8 mol % based on oxime). The result showed that the yield of ε-caprolactam is 68.87% and the value of TON is 24.8.

Example 22

Beckmann rearrangement of cyclohexanone oxime was carried out in a similar manner to Example 21 with the exception that acetic anhydride was not added. The result showed that the yield of ε-caprolactam is 30.02% and the value of TON is 10.8.

Example 23

Beckmann rearrangement of cyclohexanone oxime was carried out in a similar manner to Example 21 with the exception that a mixed liquid of N,N-dimethylformamide/toluene (25/75% volume ratio) was used instead of the mixed liquid of N,N-dimethylformamide/toluene (50/50% volume ratio). The result showed that the yield of ε-caprolactam is 52.94% and the value of TON is 19.0.

Example 24

Beckmann rearrangement of cyclohexanone oxime was carried out in a similar manner to Example 23 with the exception that acetic anhydride was not added. The result showed that the yield of ε-caprolactam is 16.53% and the value of TON is 5.9.

Table 6 shows the results of Examples 21 to 24.

TABLE 6

| | Carboxylic anhydride | DMF/toluene volume ratio | Yield of lactam (%) | Value of TON |
|---|---|---|---|---|
| Example 15 | acetic anhydride | DMF 100% | 96.44 | 17.3 |
| Example 21 | acetic anhydride | 50/50 | 68.87 | 24.8 |
| Example 22 | none | 50/50 | 30.02 | 10.8 |
| Example 23 | acetic anhydride | 25/75 | 52.94 | 19.0 |
| Example 24 | none | 25/75 | 16.53 | 5.9 |

Examples 25 to 29

Each Beckmann rearrangement of cyclohexanone oxime was carried out in a similar manner to Example 15 with the exception that a sulfonic acid or a sulfonic anhydride described in Table 7 was used instead of p-toluenesulfonic anhydride. Table 7 shows the results.

TABLE 7

| Example | Sulfonic acid/acid anhydride Compound | Sulfonic acid/acid anhydride Amount | Yield of caprolactam (%) | Value of TON |
|---|---|---|---|---|
| 25 | methanesulfonic anhydride | 0.165 g (0.950 mmol) | 95.52 | 17.1 |
| 26 | p-toluenesulfonic acid | 0.152 g (0.883 mmol) | 80.32 | 15.5 |
| 27 | p-toluenesulfonic acid H₂O | 0.169 g (0.889 mmol) | 78.45 | 15.0 |
| 28 | p-dodecylbenzene sulfonic acid | 0.301 g (0.921 mmol) | 82.16 | 15.1 |
| 29 | methanesulfonic acid | 0.090 g (0.933 mmol) | 74.80 | 13.8 |

INDUSTRIAL APPLICABILITY

According to the process of the present invention, an amide compound can be produced in high yields from an oxime compound under mild reaction conditions, and therefore, the process is advantageous for the industrial production.

While the invention has been described in detail and with reference to specific embodiments thereof, it will be apparent to one skilled in the art that various changes and modifications can be made therein without departing from the spirit and scope thereof.

This application is based on Japanese patent applications No. 2000-121619 filed on Apr. 21, 2000, No. 2000-372301 filed on Dec. 7, 2000 and No. 2000-372302 filed on Dec. 7, 2000, the entire contents thereof being hereby incorporated by reference.

What is claimed is:

1. A process for producing an amide compound by subjecting an oxime compound to Beckmann rearrangement in a liquid phase, wherein the reaction is carried out in the presence of a non-fluorine-containing sulfonic anhydride and an N,N-disubstituted amide compound.

2. The process for producing an amide compound according to claim 1, wherein the non-fluorine-containing sulfonic anhydride is a sulfonic anhydride selected from aromatic sulfonic anhydrides and aliphatic sulfonic anhydrides.

3. The process for producing an amide compound according to claim 2, wherein the non-fluorine-containing sulfonic anhydride is a benzensulfonic anhydride or an alkylsulfonic anhydride which may have a substituent.

4. The process for producing an amide compound according to claim 3, wherein the non-fluorine-containing sulfonic anhydride is p-toluenesulfonic anhydride or methanesulfonic anhydride.

5. The process for producing an amide compound according to claim 1, wherein the non-fluorine-containing sulfonic anhydride is used in an amount ranging from 0.2 to 20 mol % based on the oxime compound.

6. The process for producing an amide compound according to claim 1, wherein the N,N-di substituted amide compound is used in a molar ratio ranging from 10 to 2000 relative to the non-fluorine-containing aromatic sulfonic anhydride.

7. The process for producing an amide compound according to claim 1, wherein the N,N-disubstituted amide compound is an N,N-dialkylformamide.

8. The process for producing an amide compound according to claim 1, wherein the N,N-disubstituted amide compound is used in an amount of 2 to 100 times by weight as much as the oxime compound.

9. The process for producing an amide compound according to claim 1, wherein a solvent selected from aromatic hydrocarbon compounds is used as a reaction solvent.

10. the process for producing an amide compound according to claim 9, wherein the solvent selected from aromatic hydrocarbon compounds is used in an amount of 0.01 to 20 times by volume as much as the N,N-disubstituted amide compound.

11. The process for producing an amide compound according to claim 1, wherein the oxime compound is a cyclic oxime compound.

12. The process for producing an amide compound according to claim 1, wherein the oxime compound is cyclohexanone oxime and the amide compound is ε-caprolactam.

13. The process for producing an amide compound according to claim 1, wherein the reaction temperature is a temperature within the range of 40 to 150° C.

14. A process for producing an amide compound by subjecting an oxime compound to Beckmann rearrangement in a liquid phase, wherein the reaction is carried out in the presence of at least one compound selected from the group consisting of sulfonic acids and anhydrides thereof, an N,N-disubstituted amide compound, and an carboxylic anhydride.

15. The process for producing an amide compound according to claim 14, wherein said sulfonic acids and anhydrides thereof are aromatic sulfonic acids or aliphatic sulfonic acids and anhydrides thereof.

16. The process for producing an amide compound according to claim 15, wherein said sulfonic acids are benzenesulfonic acids or alkylsulfonic acids which may have a substituent.

17. The process for producing an amide compound according to claim 16, wherein the at least one compound selected from the group consisting of sulfonic acids and anhydrides thereof is selected from p-toluenesulfonic anhydride, methanesulfonic anhydride, p-toluenesulfonic acid, p-toluenesulfonic acid monohydrate, and methanesulfonic acid.

18. The process for producing an amide compound according to claim 14, wherein the at least one compound selected from the group consisting of sulfonic acids and anhydrides thereof is used in an amount ranging from 0.2 to 20 mol % based on the oxime compound.

19. The process for producing an amide compound according to claim 14, wherein the N,N-disubstituted amide compound is used in a molar ratio ranging from 10 to 2000 relative to at least one compound selected from the group consisting of sulfonic acids and anhydrides thereof.

20. The process for producing an amide compound according to claim 14, wherein the carboxylic anhydride is an alkylcarboxylic anhydride having 1 to 4 carbon atoms.

21. The process for producing an amide compound according to claim 14, wherein the N,N-disubstituted amide compound is an N,N-dialkylformamide.

22. The process for producing an amide compound according to claim 14, wherein the N,N-disubstituted amide compound is used in an amount of 2 to 100 times by weight as much as the oxime compound.

23. The process for producing an amide compound according to claim 14, wherein a solvent selected from aromatic hydrocarbon compounds is used as a reaction solvent.

24. The process for producing an amide compound according to claim 23, wherein the solvent selected from aromatic hydrocarbon compounds is used in an amount of 0.01 to 20 times by volume as much as the N,N-disubstituted amide compound.

25. The process for producing an amide compound according to claim 14, wherein the oxime compound is a cyclic oxime compound.

26. The process for producing an amide compound according to claim 14, wherein the oxime compound is cyclohexanone oxime and the amide compound is ε-caprolactam.

27. The process for producing an amide compound according to claim 14, wherein the reaction temperature is a temperature within the range of 40 to 150° C.

* * * * *